(12) United States Patent
Porter et al.

(10) Patent No.: US 10,835,392 B2
(45) Date of Patent: Nov. 17, 2020

(54) TRANSDERMAL INTRAOSSEOUS DEVICE

(71) Applicant: Biomet Manufacturing, LLC, Warsaw, IN (US)

(72) Inventors: Joshua R. Porter, Winona Lake, IN (US); Troy W. Hershberger, Winona Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 78 days.

(21) Appl. No.: 15/921,444

(22) Filed: Mar. 14, 2018

(65) Prior Publication Data

US 2018/0200081 A1    Jul. 19, 2018

Related U.S. Application Data

(63) Continuation of application No. 14/703,024, filed on May 4, 2015, now Pat. No. 9,949,848, which is a
(Continued)

(51) Int. Cl.
*A61F 2/60* (2006.01)
*A61F 2/50* (2006.01)
(Continued)

(52) U.S. Cl.
CPC .............. *A61F 2/60* (2013.01); *A61F 2/78* (2013.01); *A61F 2/28* (2013.01); *A61F 2/2814* (2013.01); *A61F 2/30749* (2013.01); *A61F 2002/5083* (2013.01); *A61F 2002/607* (2013.01); *A61F 2002/7887* (2013.01); *A61F 2220/0008* (2013.01); *A61F 2250/006* (2013.01); *A61F 2250/0064* (2013.01)

(58) Field of Classification Search
CPC ....................................................... A61F 2/2814
See application file for complete search history.

(56) References Cited

U.S. PATENT DOCUMENTS

| | | |
|---|---|---|
| 3,947,897 A | 4/1976 | Owens |
| 4,158,895 A | 6/1979 | Frosch et al. |

(Continued)

OTHER PUBLICATIONS

"Amputee Implant Devices-Osseointegration", informational website [Online]. Retrieved from the Internet: <http://www.amouteeimolantdevices.com>, (Jun. 4, 2014), 2 pgs.
(Continued)

*Primary Examiner* — Jacqueline Woznicki
(74) *Attorney, Agent, or Firm* — Schwegman Lundberg & Woessner, P.A.

(57) ABSTRACT

A transdermal intraosseous device for coupling a bone stump to an external prosthetic device includes a bone fixator, an external connector and a plurality of modular interface components. The bone fixator includes a proximal portion configured for anchoring into the bone stump of the patient and a distal portion including a base collar configured for subcutaneous implantation. The external connector has a distal portion for coupling to the external prosthetic device and a proximal portion for coupling to the distal portion of the bone fixator. Each interface component can be removably coupled to the base collar and has different size and shape to provide a surgeon-selected transition between the prosthetic device and the patient's skin.

16 Claims, 10 Drawing Sheets

Related U.S. Application Data continuation of application No. 13/756,040, filed on Jan. 31, 2013, now Pat. No. 9,023,115.

(51) Int. Cl.
*A61F 2/78* (2006.01)
*A61F 2/28* (2006.01)
*A61F 2/30* (2006.01)

(56) References Cited

U.S. PATENT DOCUMENTS

| | | | |
|---|---|---|---|
| 6,197,065 | B1 | 3/2001 | Martin et al. |
| 6,508,841 | B2 | 1/2003 | Martin et al. |
| 6,712,855 | B2 | 3/2004 | Martin et al. |
| 6,869,450 | B2 | 3/2005 | Grundei |
| 7,014,661 | B2 | 3/2006 | Blunn et al. |
| 7,141,073 | B2 | 11/2006 | May et al. |
| 7,476,254 | B2 | 1/2009 | White et al. |
| 7,722,678 | B2 | 5/2010 | Brown et al. |
| 8,512,416 | B2 | 8/2013 | Porter et al. |
| 9,023,115 | B2 | 5/2015 | Porter et al. |
| 9,949,848 | B2 | 4/2018 | Porter et al. |
| 2003/0109878 | A1 | 6/2003 | Grundei |
| 2006/0149254 | A1* | 7/2006 | Lauryssen ............ A61F 2/4405 606/247 |
| 2007/0060891 | A1 | 3/2007 | Skiera et al. |
| 2007/0099153 | A1* | 5/2007 | Fromovich ............ A61C 8/005 433/174 |
| 2009/0149966 | A1 | 6/2009 | Blunn et al. |
| 2011/0190907 | A1 | 8/2011 | Porter et al. |
| 2013/0073057 | A1 | 3/2013 | Smith |
| 2014/0156022 | A1 | 6/2014 | Holt |
| 2014/0214177 | A1 | 7/2014 | Porter et al. |
| 2015/0305893 | A1 | 10/2015 | Porter et al. |

OTHER PUBLICATIONS

"U.S. Appl. No. 13/756,040, Examiner Interview Summary dated Oct. 31, 2014", 3 pgs.
"U.S. Appl. No. 13/756,040, Non Final Office Action dated Aug. 5, 2014", 13 pgs.
"U.S. Appl. No. 13/756,040, Notice of Allowance dated Nov. 21, 2014", 9 pgs.
"U.S. Appl. No. 13/756,040, Response filed May 6, 2014 to Restriction Requirement dated Mar. 6, 2014", 9 pgs.
"U.S. Appl. No. 13/756,040, Response filed Jul. 23, 2014 to Restriction Requirement dated May 23, 2014", 11 pgs.
"U.S. Appl. No. 13/756,040, Response filed Nov. 5, 2014 to Non Final Office Action dated Aug. 5, 2014", 11 pgs.
"U.S. Appl. No. 13/756,040, Restriction Requirement dated Mar. 6, 2014", 10 pgs.
"U.S. Appl. No. 13/756,040, Restriction Requirement dated May 23, 2014", 8 pgs.
"U.S. Appl. No. 14/703,024, Corrected Notice of Allowance dated Dec. 28, 2017", 2 pgs.
"U.S. Appl. No. 14/703,024, Examiner Interview Summary dated Mar. 13, 2017", 3 pgs.
"U.S. Appl. No. 14/703,024, Final Office Action dated Nov. 6, 2017", 6 pgs.
"U.S. Appl. No. 14/703,024, Final Office Action dated Dec. 22, 2016", 12 pgs.
"U.S. Appl. No. 14/703,024, Non Final Office Action dated Jul. 20, 2016", 16 pgs.
"U.S. Appl. No. 14/703,024, Non Final Office Action dated Aug. 4, 2017", 14 pgs.
"U.S. Appl. No. 14/703,024, Notice of Allowance dated Dec. 14, 2017", 5 pgs.
"U.S. Appl. No. 14/703,024, Preliminary Amendment filed Oct. 8, 2015", 5 pgs.
"U.S. Appl. No. 14/703,024, Response filed Mar. 20, 2017 to Final Office Action dated Dec. 22, 2016", 11 pgs.
"U.S. Appl. No. 14/703,024, Response filed May 31, 2016 to Restriction Requirement dated Apr. 15, 2016", 7 pgs.
"U.S. Appl. No. 14/703,024, Response filed Oct. 19, 2017 to Non Final Office Action dated Aug. 4, 2017", 12 pgs.
"U.S. Appl. No. 14/703,024, Response filed Nov. 28, 2016 to Non Final Office Action dated Jul. 20, 2016", 11 pgs.
"U.S. Appl. No. 14/703,024, Response filed Nov. 29, 2017 to Final Office Action dated Nov. 6, 2017", 7 pgs.
"U.S. Appl. No. 14/703,024, Restriction Requirement dated Apr. 15, 2016", 9 pgs.
"ITAP", [Online]. Retrieved from the Internet: <http://www.itao-orosthetics.com>, (Jun. 4, 2014), 1 page.
"OPRA Implant System Product Catalogue", brochure. Integrum AB, (2014), 8 pgs.
"The ILP Prosthesis", [Online]. Retrieved from the Internet: <http://www.osseointegration-germany.de/index.php/en/die-ilp-prothese2 on Jun. 4>, (Jun. 4, 2014), 4 pgs.
Collins, L M, "Prosthesis Method May Brighten Future for Amputees", Deseret News, reprint University of Utah School of Medicine. [Online]. Retrieved from the Internet: <http://medicine.utah.edu/orthopaedics/events/news/posthesismethod.htm>, (May 6, 2014), 2 pgs.

* cited by examiner

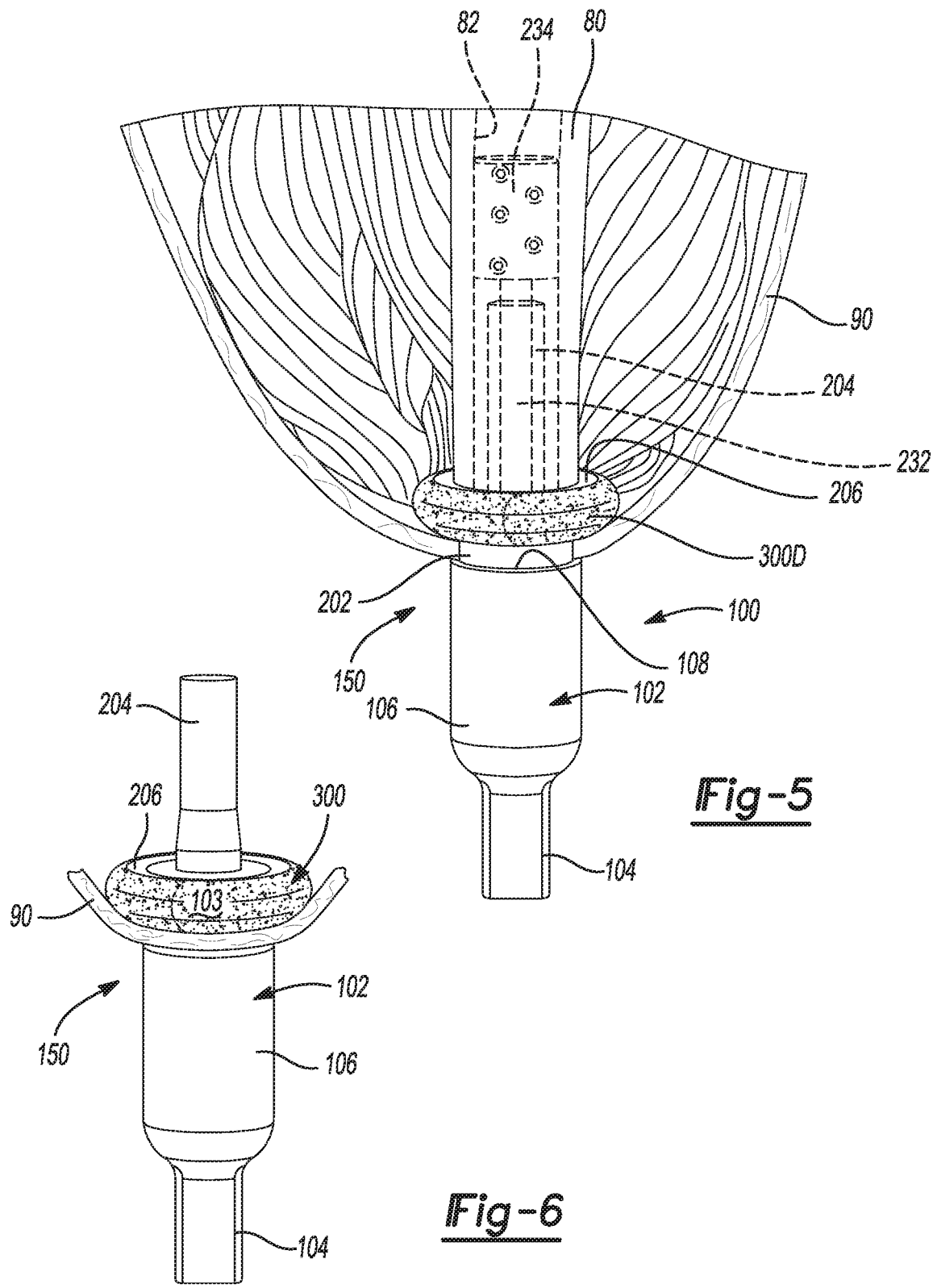

TRANSDERMAL INTRAOSSEOUS DEVICE

INTRODUCTION

Various known external fixation devices for amputation or trauma include compliant mechanisms for supporting a prosthetic device to a bone stump. In devices of this type, the compliant fixation mechanism provides a compressive stress at the bone interface for preventing bone resorption over time. Typically, a metal portion of the fixation device may extend beyond the cut surface of the bone, such that soft tissue is attached to the metal, rather than the bone. The interface between the prosthetic device and soft tissue can be a source of infection and various treatments are aimed to reduce it.

SUMMARY

The present teachings provide a transdermal intraosseous device for coupling a bone stump to an external prosthetic device and including a bone fixator, an external connector and a plurality of modular interface components. The bone fixator includes a proximal portion configured for anchoring into the bone stump of the patient and a distal portion including a base collar configured for subcutaneous implantation. The external connector has a distal portion for coupling to the external prosthetic device and a proximal portion for coupling to the distal portion of the bone fixator. Each interface component can be removably coupled to the base collar and has different size and shape to provide a surgeon-selected transition between the prosthetic device and the patient's skin.

The present teachings provide a transdermal intraosseous device for coupling a bone stump to an external prosthetic device and including a bone fixator and a modular transdermal adapter. The bone fixator includes a distal portion and a proximal portion. The proximal portion is configured for anchoring into a bone stump of the patient. The transdermal adapter includes first and second components. The first component has a proximal bore couplable to the distal portion of the bone fixator subcutaneously with a connection. The second component can be removably coupled transcutaneously to the first component.

The present teachings provide a method of implanting a transdermal intraosseous device for coupling an external prosthetic device to a bone stump. The method includes implanting a bone fixator through an intramedullary canal of the bone stump and connecting subcutaneously a first component of a transdermal adapter to a distal portion of the bone fixator. A dome-shaped portion of the first component is covered with skin from the bone stump and the skin is allowed to heal over a porous layer of the dome-shaped portion. A proximal portion of a second component of the transdermal adapter is coupled transcutaneously to the first component.

Further areas of applicability of the present teachings will become apparent from the description provided hereinafter. It should be understood that the description and specific examples are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

FIG. 5 is an environmental view of a fourth embodiment of a transdermal intraosseous device according to the present teachings, also shown in FIG. 2;

FIG. 6 is a sectional view of an embodiment of a transdermal intraosseous device showing a transdermal adapter at a first location relative to the skin the according to the present teachings;

Corresponding reference numerals indicate corresponding parts throughout the several views of the drawings.

DETAILED DESCRIPTION

The following description is merely exemplary in nature and is in no way intended to limit the present teachings, applications, or uses. Example embodiments are provided so that this disclosure will be thorough, and will fully convey the scope to those who are skilled in the art. Numerous specific details are set forth such as examples of specific components, devices, and methods, to provide a thorough understanding of embodiments of the present disclosure. It will be apparent to those skilled in the art that specific details need not be employed, that example embodiments may be embodied in many different forms and that neither should be construed to limit the scope of the disclosure. In some example embodiments, well-known processes, well-known device structures, and well-known technologies are not described in detail.

The present teachings can be used for attaching any external prosthetic device to a bone through skin via a transdermal intraosseous device. The transdermal intraosseous device can include a transdermal adapter and an intraosseous fixator. In some embodiments, the intraosseous fixator can optionally include a compliant fixator, such as, for example, the Compress® Pre-Stress Implant, which is commercially available from Biomet, Inc. Warsaw, Ind. Compliance, as used herein, is a measurement of softness as opposed to stiffness of a material. Compliance of a structural member is generally the reciprocal of Young's modulus (one dimension) or the inverse of the stiffness matrix (more than one dimensions). Accordingly, a compliant member is generally a structural member that has enhanced compliance, such as an elastic spring, bellows, Belleville washers and other elastically biasing members. The compliant fixator of the present teachings, as well as the Compress® Compliant Pre-Stress Implant, allows osseointegration at the bone/implant interface and can provide a stable, high-pressure/implant interface. The compliant fixator can also assist in the prevention of stress shielding and any concomitant bone loss.

Infection is generally a common complication with known transdermal (transcutaneous) intraosseous devices. Aggressive apical epithelial migration or epithelial downgrowth may be initiated as a normal wound-healing response to foreign bodies. If not prevented, this response may result in deep pocket formation and subsequent marsupialization of the transdermal devices. Sub-epithelial connective tissue adhesion to a transdermal intraosseous device may prevent epithelial downgrowth and associated complications, such as infection. Various other surface and/or therapeutic treatments can also be provided at the skin interface, as discussed below.

Figure 1:
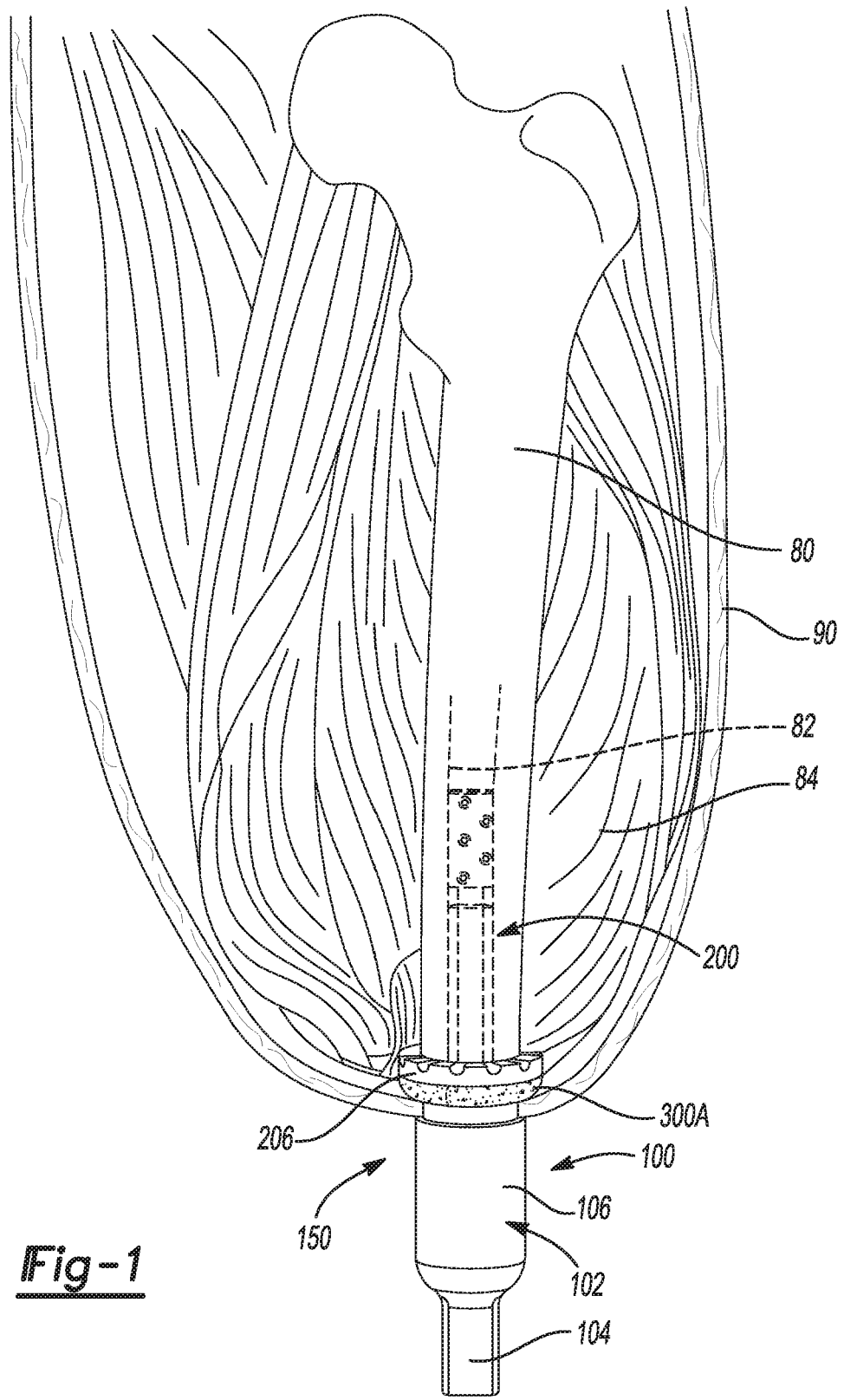
FIG. 1 is an environmental view of a first embodiment of an embodiment of a transdermal intraosseous device for a bone stump according to the present teachings.
Figure 2:
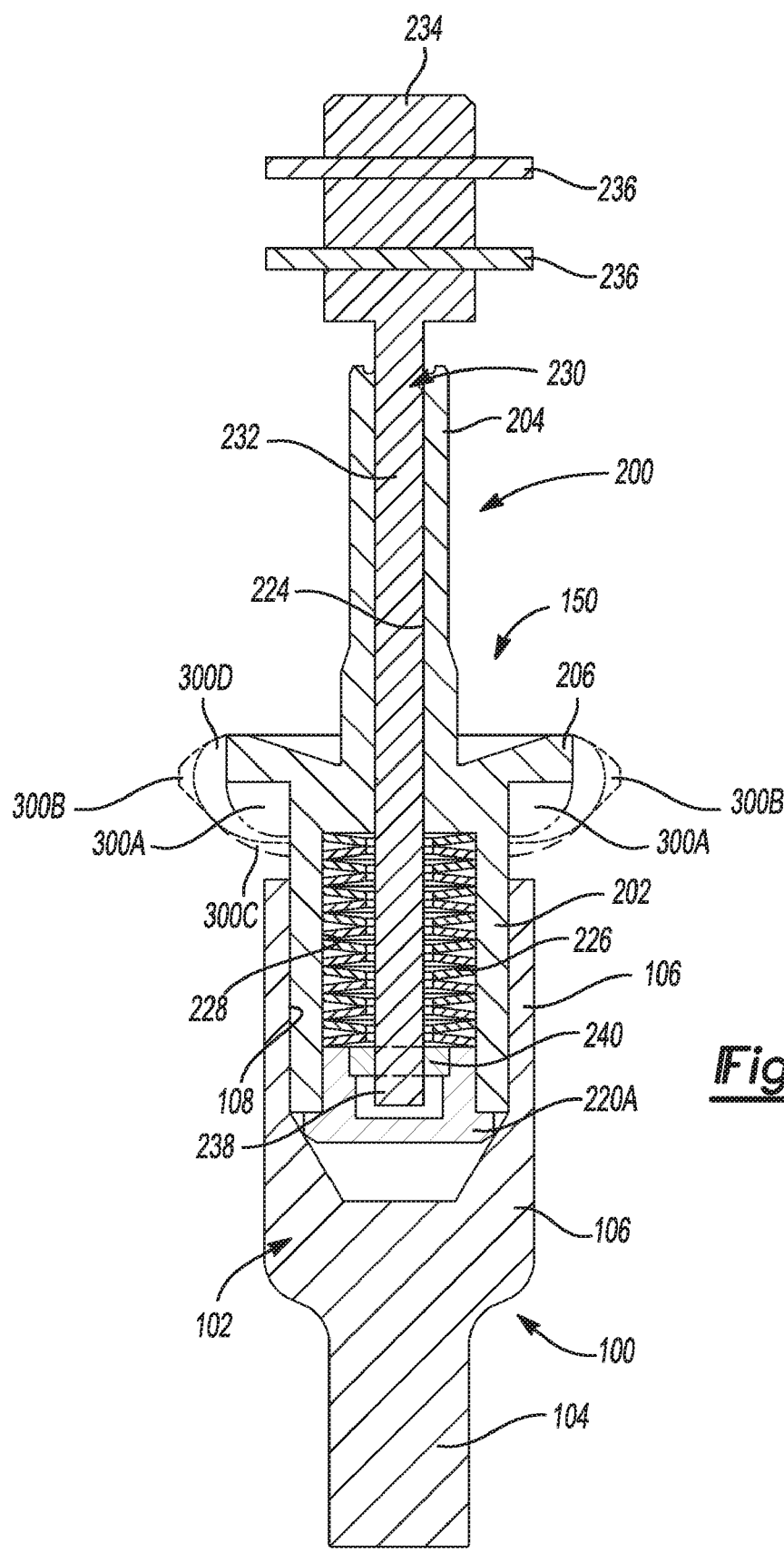
FIG. 2 is a sectional view of a transdermal intraosseous device for a bone stump according to the present teachings taken along a longitudinal central axis corresponding to the bone stump axis and illustrating in phantom lines four embodiments of a transdermal adapter of a transdermal intraosseous device, including the embodiment of FIG. 1 and the embodiments of FIGS. 3-5.

Referring to FIGS. 1 and 2, an exemplary transdermal intraosseous device 100 according to the present teachings can include an external connector 102 for connection to an external prosthetic device (not shown), a transdermal adapter 150 at the skin interface area and an intraosseous bone fixator 200 for compliant or non-compliant fixation into an intramedullary bore or IM canal 82 of a bone 80, such as a femur, tibia, humerus, etc., that is partially amputated (bone stump) and will receive the external prosthetic device. Muscle tissue is indicated at 84 and skin at 90 in FIG. 1. Accordingly, the bone fixator 200 can be a compliant fixator that can provide pre-stress to the bone or a non-compliant fixator in the form of a static (non-dynamic) anchoring member. The transdermal adapter 150 can include a porous titanium material, such as Regenerex® Porous Titanium Construct, commercially available from Biomet, Inc., Warsaw, Ind. Similarly to Regenerex®, the porous titanium material may have an average porosity of about 67 percent and pore size ranging from about 100 to about 600 microns (average of 300 microns), as well as high strength and flexibility, and could be manufactured using traditional manufacturing methods, or with additive manufacturing.

Additionally, various surface and/or therapeutic treatments can be used to improve the biocompatibility of the transdermal intraosseous device 100 at the skin interface. These treatments include, for example, the use of various anti-microbial technologies, such as silver coating, antibiotic application through surface immobilization or impregnation followed by a controlled release, diamond-like carbon coating, electrochemical processes that change the surface free energy, and highly polished titanium surfaces. Further, various biological technologies can be used to improve dermal integration of the transdermal intraosseous device 100 at the skin interface, such as functionalization of porous metal or polymer with cell adhesive peptides, proteins, macromolecules, monomers, autologous or synthetic chemokines, etc. Skin integration can also be promoted via mechanical immobilization of the skin to an in-growth surface of the transdermal intraosseous device 100 by using soft tissue clamps, sutures, screws, pads, or, alternatively, by allowing relative motion between the transdermal intraosseous device 100 and the skin at their interface. A sliding collar over a rubber or elastomer plug with antibiotic or other antimicrobial agents can used, for example, at the skin/transdermal adapter interface. Such relative motion may reduce tensile load to the healing skin site, and the elastic plug can prevent or reduce friction.

The transdermal adapter 150 can include one or more removably coupled modular interface components (300A, 300B, 300C, 300D) as well as portions of the bone fixator 200 shown at 202, 206 in FIG. 2. Accordingly, the transdermal adapter, as used herein, refers to those portions of the transdermal intraosseous device (modularly or monolithically attached) that are configured to reside at the interface of the skin with the transdermal intraosseous device 100 and adjacent areas.

As discussed above, the bone fixator 200 can be a compliant fixator configured to provide a bone biasing force to a portion of a bone. Any known compliant fixator can be used, including, but not limited to, the compliant fixators disclosed in commonly assigned U.S. Pat. Nos. 7,722,678, 7,141,073, 6,712,855, 6,508,841 and 6,197,065, all of which are assigned to common assignee Biomet Manufacturing Corp., and are incorporated herein by reference. The compliant fixator 200 is configured to provide a compressive load on the bone, thereby reducing bone loss and promoting bone growth. The compliance of the bone fixator 200 can exceed that of native bone 80, such that stress shielding does not occur. Additionally, the native bone 80 can experience physiologic dynamic compressive loading biased by a preset spring compression. In this context, evidence of bone hypertrophy or lack of bone loss may occur near the resection level resulting in increased bone strength, possibly as a result of a phenomenon known as Wolf's Law.

An exemplary compliant bone fixator 200 is illustrated in FIG. 2. The bone fixator 200 can include a distal portion 202, a proximal portion 204 and an intermediate portion in the form of a skirt-like collar 206 (base collar 206) between the distal portion 202 and the proximal portion 204. The distal portion 202 is configured to be coupled to the external connector 102 with any appropriate connection mechanism or portion, such as a taper-to-taper connection or any appropriate removable connection, as discussed below. The proximal portion 204 is an elongated tubular member received into the bore 84 of the bone 80 and is coupled to an anchoring member 230 for anchoring into the bone 80. The anchoring member 230 can include an elongated shaft 232 and an anchoring plug 234 connected to one end of the shaft 232. The anchoring plug 234 can be enlarged relative to the shaft 232 and can be fixed to the bone 80 with transverse pins or other bone screws 236. A portion of the shaft 232 opposite the plug 234 passes through a bore 224 of the proximal portion 204 of the bone fixator 200. The bore 224 of the proximal portion 204 communicates with an enlarged bore or well 228 formed in the distal portion 202 of the bone fixator 200 and configured to receive the compliant member 226.

The external connector 102 can include a distal portion 104 for connecting with the prosthetic device and an enlarged tubular proximal portion 106 having an inner bore 108 for taper to taper connection with the distal portion 202 of the bone fixator 200. The well 228 with the included compliant member 226 are accommodated in the enlarged tubular proximal portion 106 of the external connector 102.

Figure 7:
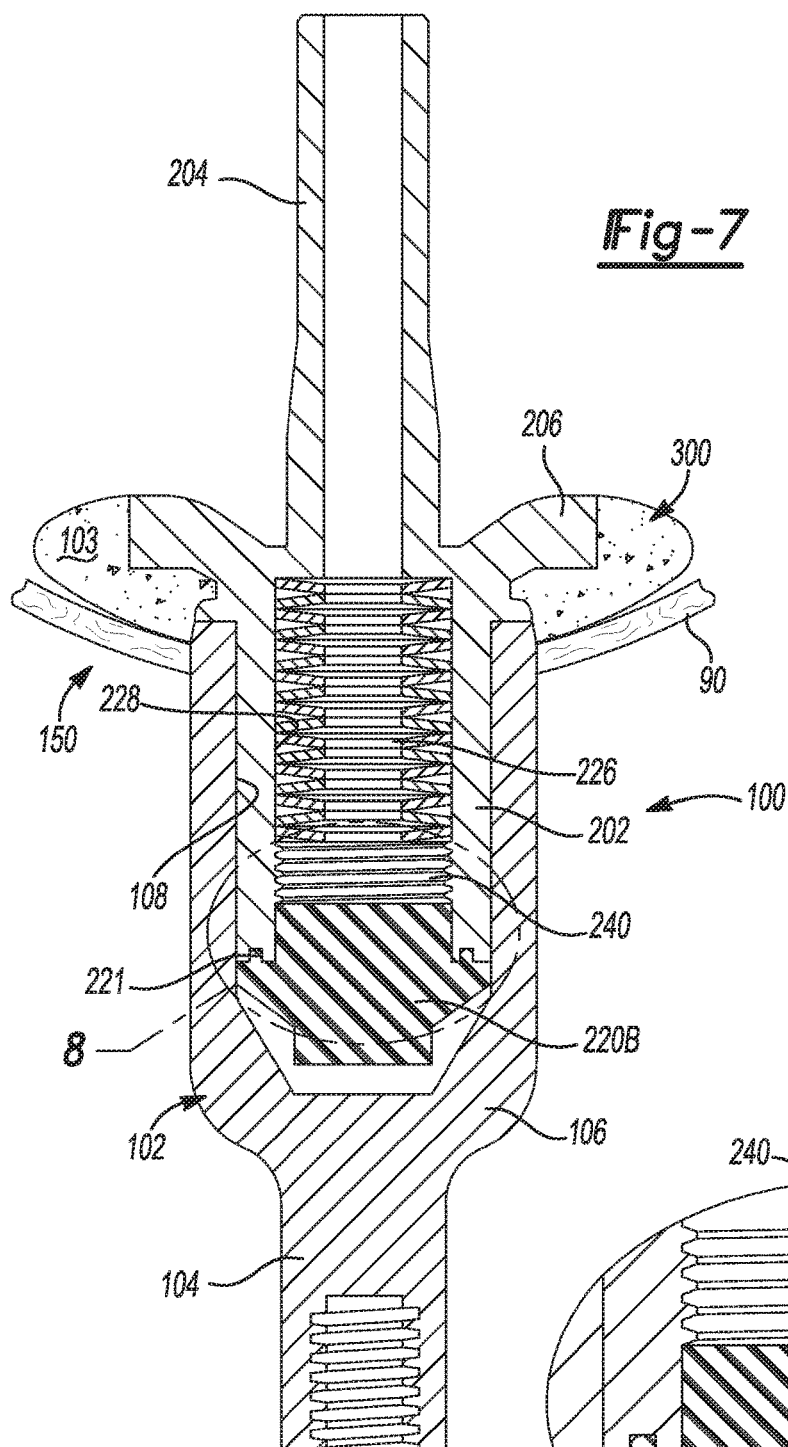
FIG. 7 is a sectional view of an embodiment of a transdermal intraosseous device showing a transdermal adapter at a second location relative to the skin according to the present teachings.

The compliant member 226 can be include one or more compliant elements, such as one or more Belleville washers, as shown in FIGS. 2 and 7 or other spring washers, or a single or double helical spring. Detailed descriptions of the structure and operation of various compliant fixators 200 and biasing mechanisms are provided in the above-referenced patents. The well 228 that receives the compliant member 226 is shaped and configured for accommodating the compliant member 226, such that the well 228 may have a larger diameter for Belleville washers than for a helical spring. The compliant bone fixator 200 can be anchored to the bone 80 and pre-stressed via the anchoring member 230. The elongated shaft 232 of the anchoring member 230 can have a threaded distal end 238. The shaft 232 can pass through the longitudinal bore 224 and through the Belleville washers, when Belleville washers are used as the compliant member 226. Alternatively, the shaft 232 can be integrally attached to the compliant member 226 and be formed as a single monolithic component, when the compliant member 226 is in the form a helical spring. The compliant bone fixator 200 can be inserted through a hole/incision punched through the skin and anchored into the bone 80 via the anchoring member 230, while the compliant member 226 is held with a temporary tubular knob (not shown). A nut 240 can be threaded on to the distal threaded portion 238 of the shaft 232 and rotated to pre-stress the compliant member 226 to a desired amount. The temporary tubular knob may then be removed and replaced optionally with a sealing plug or cap, such as cap 220A in FIG. 2, for example.

Figure 3:
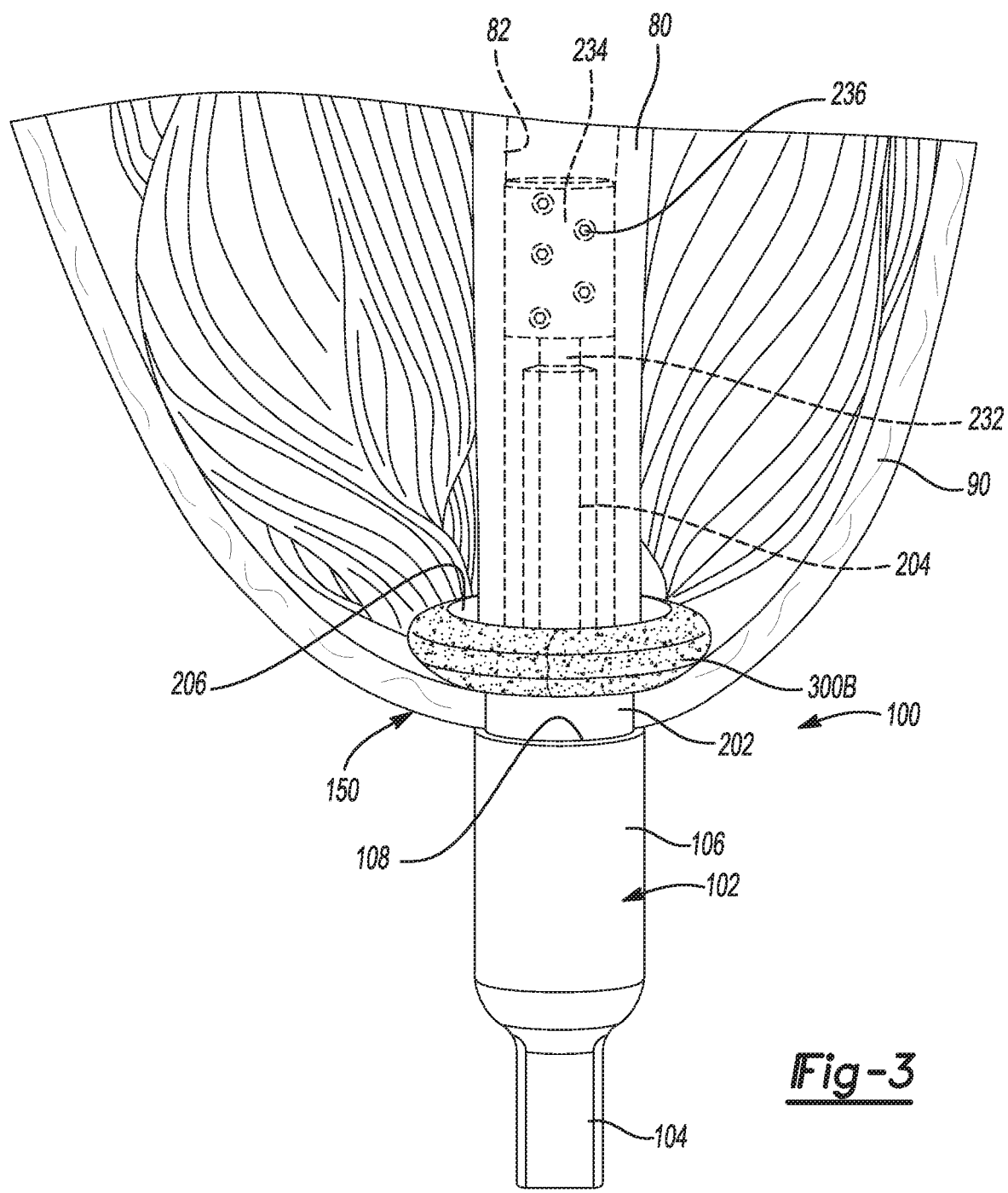
FIG. 3 is an environmental view of a second embodiment of a transdermal intraosseous device according to the present teachings, also shown in FIG. 2.
Figure 4:
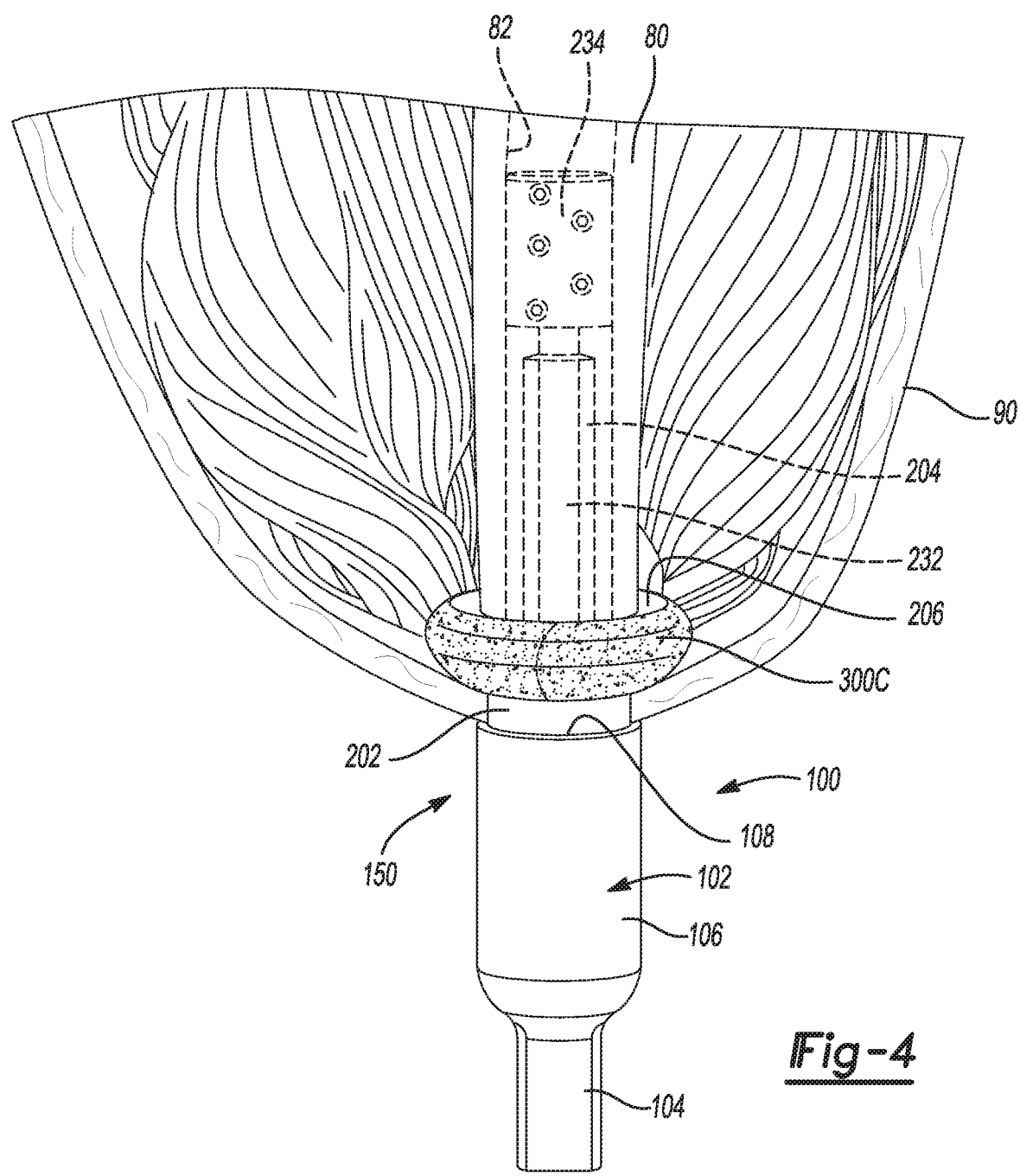
FIG. 4 is an environmental view of a third embodiment of a transdermal intraosseous device according to the present teachings, also shown in FIG. 2.

The base collar 206 can be either modularly (i.e., removably) or fixedly coupled subcutaneously to the bone fixator 200. In some embodiments, the base collar 206 or at least the surfaces of the base collar 206 that come into contact with the anatomy of the patient, can be coated with a porous titanium plasma spray with a hydroxyapatite (HAS) coating or other similar treatment for increased biologic fixation. The base collar 206 can be fixed to a resected distal surface of the bone 80 with anti-rotation pins or other fasteners through corresponding apertures. In the embodiments illustrated in FIGS. 1-5, a plurality of modular interface components designated as 300A to 300D and corresponding to FIG. 1 (300A), FIG. 3 (300B), FIG. 4 (300C) and FIG. 5 (300D) can be provided to the surgeon as a kit and a surgeon-selected selected interface component can be placed over the base collar 206 and attached thereto. The relative geometry of the modular interface components 300A-300D is illustrated in FIG. 2, with the outer surfaces of the modular interface components 300A-300D illustrated using different lines. Each of the modular interface components 300A-300D includes two semi-annular portions (right and left side) that can be coupled or snapped on the base collar 206 with any type of connector mechanism or quick connector device or arrangement, such as, for example, dovetail connectors, tongue and groove connectors, taper junction connectors, or screws. Each interface component 300A to 300D can be removably coupled to the base collar subcutaneously. Different sizes and shapes are provided for surgeon selection or customized per surgeon's specifications to provide a surgeon-selected transition between the external prosthetic device and the patient's skin 90.

The external adapter 102 and the bone fixator 200 can be made from a biocompatible metal, such as polished titanium alloy (Ti-6-4). The modular interface components 300A-300D can also be made of titanium alloy or other metal and can be coated with a porous structure or coating 103 to improve biocompatibility at the skin interface. The porous coating or layer 103 may include a porous metal structure, such as the Regenerex® Porous Titanium Construct discussed above. The porous coating 103 can include a roughness treatment formed by blasting, including ceramic bead blasting, sand blasting, grit blasting and similar treatments. Acid etching, such as an Osseotite® treatment can also be used. Osseotite® is a surface treatment commercially available from Biomet, Inc., Warsaw, Ind.

The transdermal intraosseous device 100 can be impacted in position for locking the tapered connection between the external connector 102 and the distal portion 202 of the bone fixator 200. The skin flap around the incision can be sutured around the external portion of the intraosseous transdermal device 100.

Referring to FIGS. 1-5, several modular interface components 300A to 300D (or generically 300) are designed to accommodate optimal contact between the skin and the intraosseous transdermal device 100. Several modular interface components 300 can be provided to the surgeon or designed specifically for a patient's needs. Some the modular interface components 300 can be designed to be either partially or entirely under the patient's skin 90 and can have different dimensions and shapes as illustrated in FIGS. 1-5. The size of the surface area and the curvature of the transition at the skin interface varies among the interface components 300A to 300D, such that an appropriate interface component can be selected by the surgeon to optimize and improve initial adhesion and limit skin damage respectively for each specific patient. The semi annular or semi-toroidal shapes can include curved portions of different curvature and dimensions and, in some embodiments, planar portions.

Referring to FIG. 5 or 6 and 7, two versions of the intraosseous transdermal device 100 are compared. In FIG. 5, the taper connection between the proximal tubular portion 106 of the external connector 102 and the distal portion 202 of the bone fixator 200 terminates outside the skin and outside the porous layer 103 of the interface component 300. In contrast, in the version of FIG. 7 the taper connection extends under the skin 90 and into the porous layer 103 of the interface component 300. The geometry of FIG. 7 may provide an additional barrier against infection because the innate immune response could combat potential migration into the taper connection.

Figure 8:
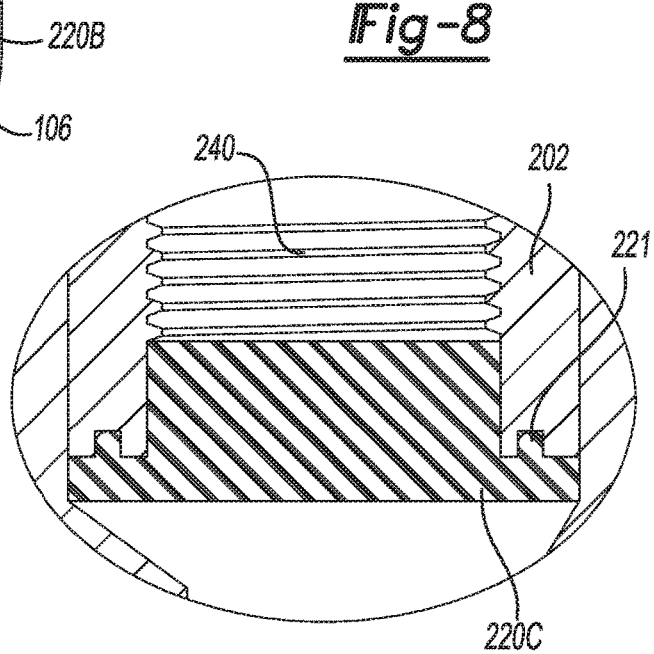
FIG. 8 is an alternative embodiment of a corresponding detail of FIG. 7.
Figure 9:
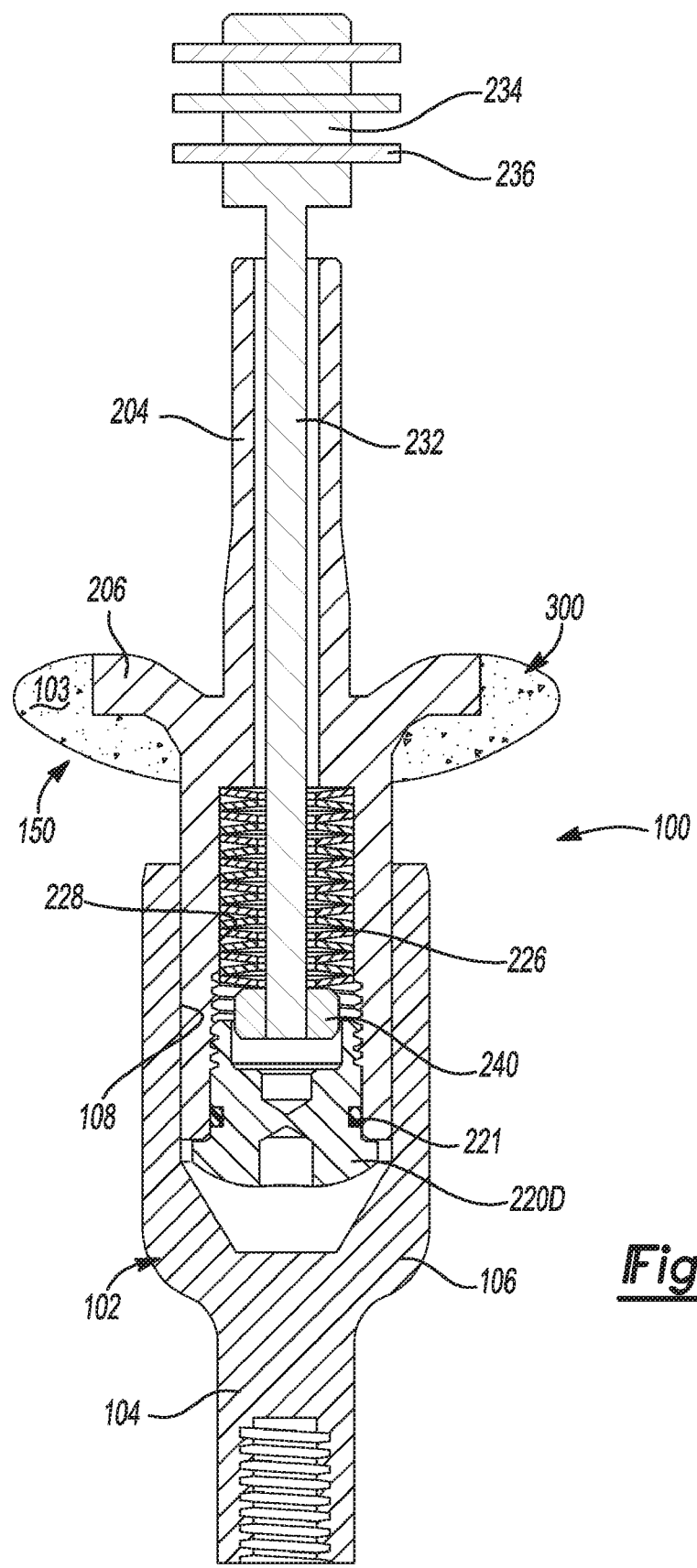
FIG. 9 is a sectional view of another embodiment of a transdermal intraosseous device according to the present teachings.

Referring to FIGS. 7, 8 and 9, another barrier against microbial infiltration can be provided by incorporating a gasket or plug 220B, 220C, and 220D of medical grade elastomer, such as silicone, having an interference fit with the well 228 that houses the compliant member 226. An O-ring 221 can provide an additional barrier to seal the intramedullary canal 82 of the bone 80. Three different geometries of the plug 220B, 2200, 220D are illustrated in FIGS. 7, 8 and 9 (only the relevant detail is shown in FIG. 8). The silicone O-rings could have multiple placement options. For example, while a single O-ring 221 is illustrated in FIGS. 7-9, multiple O-rings 221 can be used where placement can exemplary be a combination of that shown in FIGS. 7-9. In this regard, an O-ring 221 can be positioned in a groove formed in the distal portion 202 of the base fixator 200 as shown in FIGS. 7-8 and/or a groove can be formed as shown in the plug 220D of FIG. 9 for receipt of O-ring 221. Alternatively, the placement of the grooves can also be reversed, where the groove is formed directly opposite to the illustrated position for receipt of the O-ring 221. In other words, the groove can be found in either the plug 220 or the distal portion 202 at the illustrated locations or any other locations.

Figure 10:
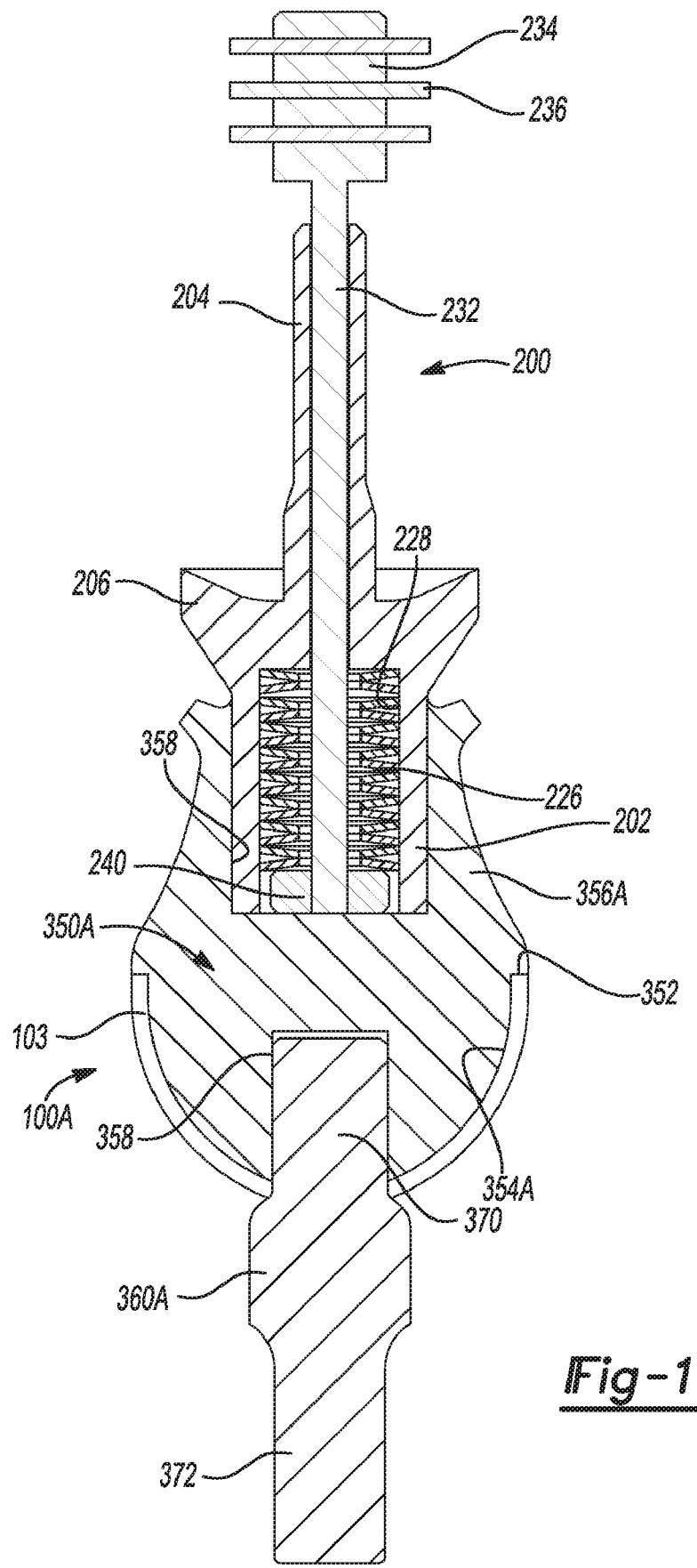
FIG. 10 is a sectional view of another embodiment of a transdermal intraosseous device for a two-stage procedure according to the present teachings.
Figure 11:
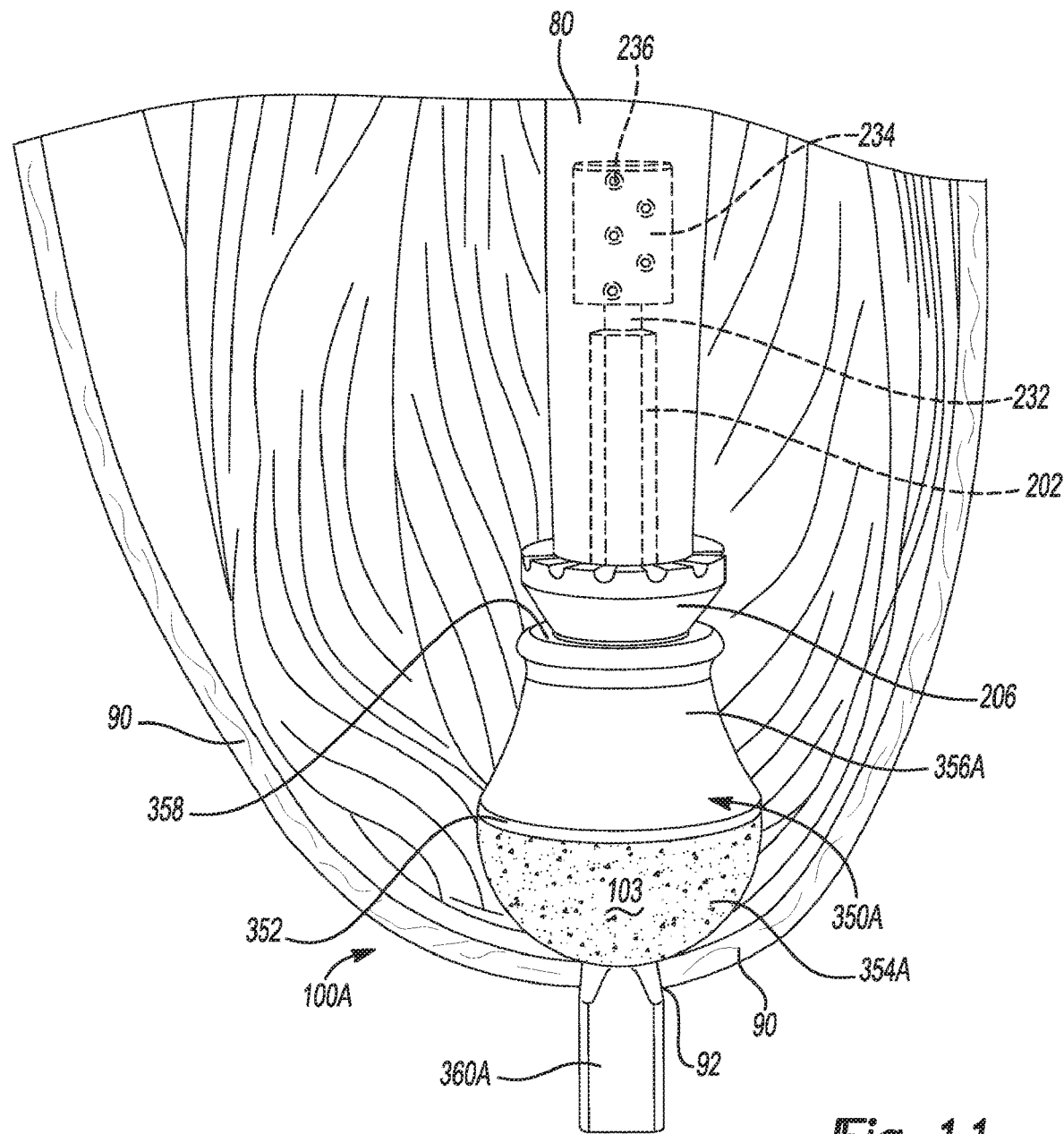
FIG. 11 is an environmental view of transdermal intraosseous device of FIG. 10.
Figure 12:
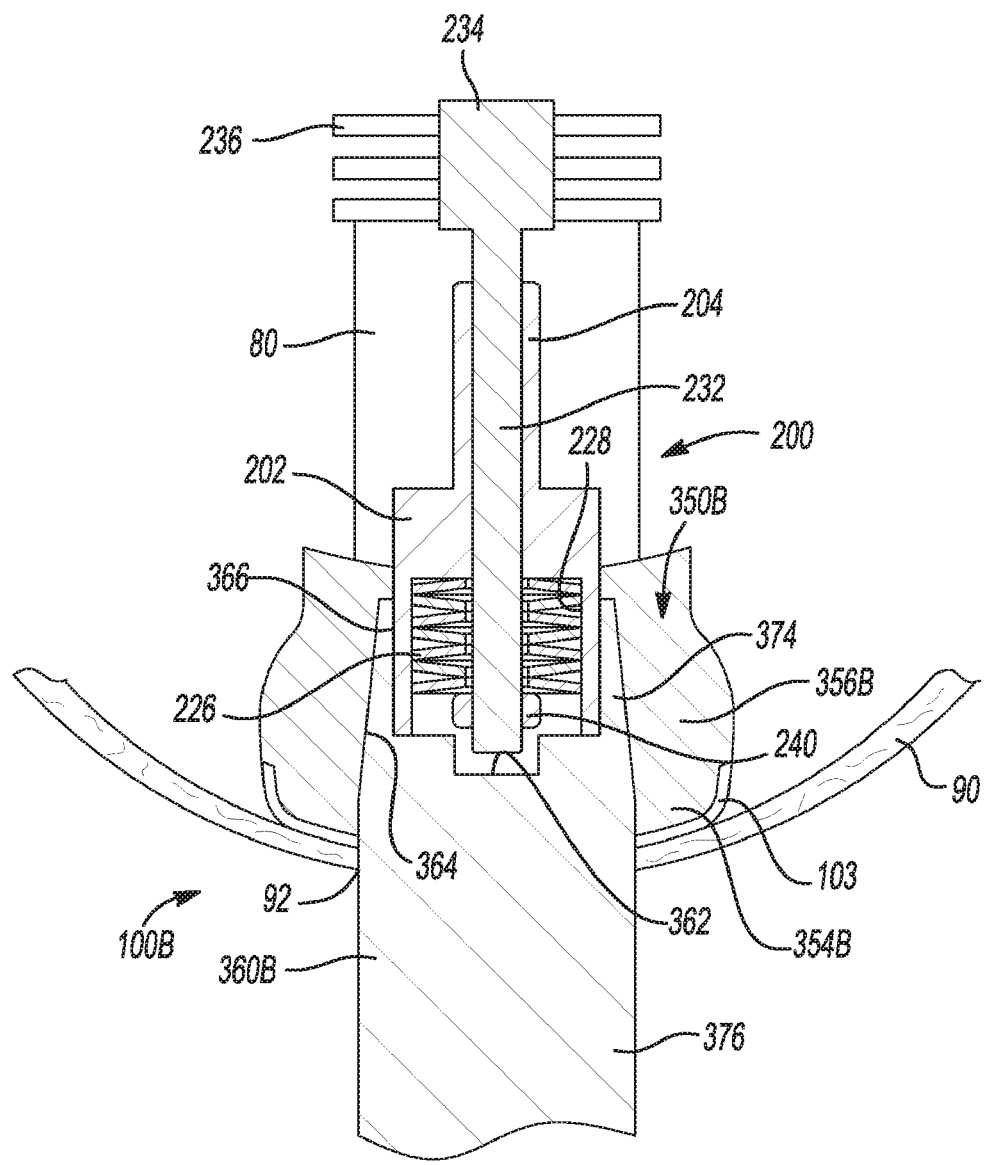
FIG. 12 is a sectional view of another embodiment of a transdermal intraosseous device for a two-stage procedure according to the present teachings.

Referring to FIGS. 10-12, two versions of a transdermal intraosseous device 100A, 100B for a two-stage surgical procedure are illustrated. In these embodiments, the compliant member 226 of the bone fixator 200 is accommodated subcutaneously, i.e., under the skin 90 of the patient, as discussed below. Corresponding elements of the bone fixator 200 are referenced with the same numerals as in FIGS. 1-9 and their description is not repeated.

Each of the transdermal intraosseous devices 100A, 100B includes a corresponding modular transdermal adapter 350A, 350B that includes, respectively a first component 356A, 356B and a second component 360A, 360B removably coupled to one another. The first components 356A, 356B are subcutaneous and are implanted during the first stage and coupled to the distal portion 202 of the bone fixator 200 by any appropriate connection mechanism such as by a taper-to-taper connection, as in the embodiments discussed in FIGS. 1-9. The skin 90 is closed by the surgeon over a porous layer 103 of the first component 356A, 356B and allowed to heal and integrate with the porous layer 103, before the second stage of the surgical procedure. The second components 360A, 360B are transcutaneous and coupled to the corresponding first components 356A, 356B during the second stage of the procedure, as discussed below. At the second stage, an opening 92 is made in the skin with a scalpel or a biopsy punch and the second component 360A, 360B is coupled to the corresponding first component 356A. 356B with another taper-to-taper connection or other type of removable connection, such a threaded connection, for example.

More specifically, and referring to FIGS. 10 and 11, the first component 356A of the transdermal adapter 350A includes a dome-shaped portion 354A that can be partially coated with a coating layer 103 up to a circumference 352 for promoting skin adhesion and biological integration. The first component 356A has a proximal tapered bore 358 that receives the tapered distal portion 202 of the bone fixator 200, and a distal tapered bore 358 coupled with a proximal portion 370 of the second component 360A with a taper-to-taper connection. Other types of removable connections can also be used. The compliant member 226 is received in the bore 228 of the distal portion 202 of the bone fixator 200, such that the compliant member 226 is accommodated subcutaneously in the appropriately-sized bore 358 of the first component 356A and in a proximal portion of the transdermal adapter 350A. A distal portion or external connector 372 of the second component 360A can be coupled to an external prosthetic device for the bone stump of the patient.

Referring to FIG. 12, the first component of the 356B of the transdermal adapter 350B has a dome-shaped or rounded portion 354B and is partially coated with a coating layer 103 at the skin interface for promoting skin adhesion and biological integration. The first component 356B has a distal tapered bore 364 that receives a tapered end of the second component 360B with a taper-to-taper connection, although other types of removable connections can also be used. The second component 360B has a tubular proximal portion 374 with a proximal tapered bore 366 that receives the tapered distal portion 202 of the bone fixator 200 and forms a well 362 for the compliant member 26 and nut 240 at the distal portion 202 of the bone fixator 200. Accordingly, the compliant member 226 is also accommodated subcutaneously in a proximal portion of the transdermal adapter 350B. A distal portion 376 of the second component 360B can be coupled to an external prosthetic device for the bone stump of the patient.

Summarizing, the transdermal intraosseous devices of FIGS. 10-12 allow the surgeon to use a two-stage surgical procedure. During the first stage, only the first component (356A, 356B) of the transdermal adapter (350A, 350B) is implanted subcutaneously and coupled to the bone fixator 200. The skin at the interface (a skin flap of the bone stump) is closed over the porous layer 103 of the subcutaneous first component (356A, 356B). After the wound from the first stage of the surgical procedure has healed, the interfacial skin is punctured to create an opening 92 to couple transcutaneously the second component (360A, 360B) to first component (356A, 356B).

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A transdermal intraosseous device configured for coupling a bone stump of a patient to an external prosthetic device comprising:
   a bone fixator comprising:
      a distal portion including a tapered portion and a well including a compliant member therein, the distal portion configured to terminate external to skin of the patient;
      a proximal portion configured for anchoring into the bone stump of the patient; and
      a base collar configured for subcutaneous implantation adjacent to the bone stump;
   an external connector comprising:
      a proximal portion including a tapered bore configured to receive the tapered portion of the distal portion of the bone fixator to releasably couple the external connector to the bone fixator; and
      a distal portion couplable to the external prosthetic device;
   a sealing plug disposable in the well and at least partially in the bore of the external connector; and
   a modular interface component located proximal of the external component and proximal of the distal portion of the bone fixator, the modular interface component removably coupled to the base collar of the bone fixator.

2. The transdermal intraosseous device of claim 1, wherein the modular interface component is coated with a porous titanium plasma spray and a hydroxyapatite coating configured to increase biologic fixation.

3. The transdermal intraosseous device of claim 1, wherein the base collar is configured for fixation to a resected distal surface of the bone stump.

4. The transdermal intraosseous device of claim 3, wherein the base collar is configured for fixation to the bone stump using anti-rotation pins passing through corresponding apertures of the base collar.

5. The transdermal intraosseous device of claim 1, wherein the modular interface component is shaped to accommodate optimal contact between the modular interface component and skin of the patient.

6. A transdermal intraosseous device configured for coupling a bone stump of a patient to an external prosthetic device comprising:
   a bone fixator comprising:
      a distal portion including a tapered portion and a well including a compliant member therein;

a proximal portion configured for anchoring into the bone stump of the patient; and a base collar configured for subcutaneous implantation adjacent to the bone stump;

an external connector comprising:

a proximal portion including a tapered bore configured to receive the tapered portion of the distal portion of the bone fixator to releasably couple the external connector to the bone fixator; and a distal portion couplable to the external prosthetic device;

a sealing plug disposable in the well and at least partially in the bore of the external connector; and a modular interface component removably coupled to the base collar of the bone fixator.

7. The transdermal intraosseous device of claim 6, wherein the modular interface component is coated with a porous titanium plasma spray and a hydroxyapatite coating configured to increase biologic fixation.

8. The transdermal intraosseous device of claim 6, wherein the base collar is configured for fixation to a resected distal surface of the bone stump.

9. The transdermal intraosseous device of claim 8, wherein the base collar is configured for fixation to the bone stump using anti-rotation pins passing through corresponding apertures of the base collar.

10. The transdermal intraosseous device of claim 6, wherein the modular interface component is shaped to promote contact between the modular interface component and skin of the patient.

11. The transdermal intraosseous device of claim 10, wherein the modular interface component further comprises two semi-annular portions couplable to the base collar.

12. The transdermal intraosseous device of claim 10, wherein the modular interface component further comprises two semi-annular portions couplable to the base collar.

13. The transdermal intraosseous device of claim 6, wherein the modular interface component is configured to be coupled to the base collar using a quick connector device.

14. The transdermal intraosseous device of claim 13, wherein the quick connector device is selected from the group consisting of a dovetail connector, a tongue and groove connector, and a taper junction connector.

15. The transdermal intraosseous device of claim 14, wherein the modular interface component is configured to be removably coupled, subcutaneously, to the base collar.

16. The transdermal intraosseous device of claim 6, wherein the modular interface component is comprised of a titanium alloy coated with a porous structure configured to promote biocompatibility at a skin interface between the modular interface component and skin of the patient.

* * * * *